United States Patent
Arai et al.

(10) Patent No.: US 10,456,597 B2
(45) Date of Patent: Oct. 29, 2019

(54) MULTILEAF COLLIMATOR AND RADIATION TREATMENT DEVICE

(71) Applicant: Hitachi, Ltd., Tokyo (JP)

(72) Inventors: Satoshi Arai, Tokyo (JP); Akihiro Miyamoto, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 318 days.

(21) Appl. No.: 15/547,359

(22) PCT Filed: Jan. 29, 2015

(86) PCT No.: PCT/JP2015/052528
§ 371 (c)(1),
(2) Date: Jul. 28, 2017

(87) PCT Pub. No.: WO2016/121051
PCT Pub. Date: Aug. 4, 2016

(65) Prior Publication Data
US 2018/0021596 A1   Jan. 25, 2018

(51) Int. Cl.
*A61N 5/10* (2006.01)
(52) U.S. Cl.
CPC ............. *A61N 5/1045* (2013.01); *A61N 5/10* (2013.01); *A61N 5/1077* (2013.01)
(58) Field of Classification Search
CPC ....... A61N 5/1045; A61N 5/10; A61N 5/1077
See application file for complete search history.

(56) References Cited

U.S. PATENT DOCUMENTS

| 4,868,843 A * | 9/1989 | Nunan ................... G21K 1/046 378/152 |
| 7,763,865 B2 * | 7/2010 | Creed ................... A61N 5/1042 250/491.1 |

FOREIGN PATENT DOCUMENTS

| EP | 0259989 A1 | 3/1988 |
| JP | 2003-210595 A | 7/2003 |
| JP | 2008-068092 A | 3/2008 |
| JP | 2009-034443 A | 2/2009 |
| JP | 2009-160055 A | 7/2009 |
| JP | 4436340 B | 3/2010 |

OTHER PUBLICATIONS

Extended European Search Report for application No. 15879948.6, dated Oct. 4, 2018, 7 pages.
International Search Report received for PCT Patent Application No. PCT/JP2015/052528 dated Apr. 28, 2015, 7 pages.

* cited by examiner

*Primary Examiner* — Hugh Maupin

(57) ABSTRACT

This multileaf collimator is provided with multiple leaves which limit the area irradiated by a radiation beam and which are arranged in the thickness direction. Each of the leaves is provided with a protruded portion which is formed protruding towards a first surface of the leaf, a depressed portion which is formed in the second surface of the leaf and into which the protruded portion formed on another leaf is inserted, a first curved surface which is formed between the first surface of the leaf and the lateral surface of the protruded portion, and a second curved surface which is formed between the second surface of the leaf and the lateral surface of the depressed portion.

6 Claims, 11 Drawing Sheets

MULTILEAF COLLIMATOR AND RADIATION TREATMENT DEVICE

CROSS-REFERENCE TO RELATED APPLICATIONS

This application is a national phase claiming the benefit of and priority to International Patent Application No. PCT/JP2015/052528, entitled "MULTILEAF COLLIMATOR AND RADIATION TREATMENT DEVICE" filed Jan. 29, 2015, which is hereby incorporated by reference in its entirety.

TECHNICAL FIELD

The present invention relates to a multileaf collimator for regulating a field irradiated by a radiation beam to conduct a radiation treatment, and to a radiation treatment apparatus using the multileaf collimator.

BACKGROUND

Tumor treatment methods include, as one method for treating a tumor, radiation treatments of irradiating an affected site with a radiation beam. In the radiation treatments, it is desirable to effectively irradiate the affected site with the radiation beam while minimizing an irradiated dose of the radiation beam (a dose) applied to a patient.

To achieve this, there have been used multileaf collimators for regulating a field of irradiation which is a radiation region/a radiation shape of a radiation beam.

Such a multileaf collimator includes a plurality of leaves in the shape of thin plates. The leaves are, in a frame, arranged side by side and spaced from each other along a plate thickness direction of the leaves. Further, each of the leaves is configured to be independently movable by means of a drive mechanism, and therefore allowed to be individually advanced into or retreated from the radiation region of the radiation beam. When the leaves are positioned in the radiation region, the radiation beam is screened by the leaves, to thereby regulate the field of irradiation. That is, regulating the field of irradiation can achieve formation of a field irradiated with the radiation beam adjusted for each patient.

In the multileaf collimator, it is necessary that the radiation beam should be prevented from leaking through a gap between leaves adjacent to each other. Patent Literature 1 discloses a structure in which a protrusion is provided to a first surface of a leaf and a groove is provided to a second surface of the leaf. In this structure, the protrusion on a first one of mutually adjacent leaves is inserted into the groove in a second one of the mutually adjacent leaves. This structure can function to prevent leakage of the radiation beam through a space between the mutually adjacent leaves.

CITATION LIST

Patent Literature

Patent Literature 1: Japan Patent No. 4,436,340 B

SUMMARY

Technical Problem

In radiation treatment apparatuses, it has been desired to further improve resolutions of the apparatuses. In order to enhance a resolution, the thickness of leaves in a multileaf collimator should be minimized.

However, when the leaves are reduced in thickness, such a thinned leaf tends to be easily cracked or broken due to stress concentrated in stepped regions (corner parts) provided to form a protrusion and a groove in the leaf.

An object of the present invention is to provide a multileaf collimator whose resolution is enhanced while minimizing leakage of a radiation beam and preventing occurrence of a crack or breakage of a leaf, and provide a radiation treatment apparatus.

Solution to Problem

According to a first aspect of the present invention, there is provided a multileaf collimator for regulating a range irradiated by a radiation beam. The multileaf collimator is equipped with a plurality of leaves arranged along the thickness direction. Each of the leaves includes a protruded portion protrudingly formed on a first side surface of the leaf and a depressed portion formed in a second side surface of the leaf and configured to receive insertion of the protruded portion formed in another one of the leaves. Each of the leaves further includes a first curved surface formed between the first side surface in a plate thickness direction of the leaf and a lateral surface of the protruded portion, and a second curved surface formed between the second side surface in the plate thickness direction of the leaf and a lateral surface of the depressed portion.

According to a second aspect of the present invention, in the multileaf collimator according to the first aspect, when a gap $g1$ between two leaves, among the plurality of leaves, arranged side by side in the thickness direction, and a gap $g2$ between the lateral surface of the depressed portion in a first one of the two leaves and the lateral surface of the protruded portion in a second one of the two leaves satisfy a relationship of $g1 \leq g2$, a radius $R$ of curvature of the first curved surface and the second curved surface may be defined to satisfy a relationship of $R \leq g1$.

According to a third aspect of the present invention, in the multileaf collimator according to the first aspect, when a gap $g1$ between two leaves, among the plurality of leaves, arranged side by side in the thickness direction and a gap $g2$ between the lateral surface of the depressed portion in a first one of the two leaves and the lateral surface of the protruded portion in a second one of the two leaves satisfy a relationship of $g2 \leq g1$, a radius $R$ of curvature of the first curved surface and the second curved surface may be defined to satisfy a relationship of $R \leq g2$.

According to a fourth aspect of the present invention, in the multileaf collimator according to the first aspect, when a gap $g1$ between two leaves, among the plurality of leaves, arranged side by side in the thickness direction and a gap $g2$ between the lateral surface of the depressed portion in a first one of the two leaves and the lateral surface of the protruded portion in a second one of the two leaves meet a relationship of $g1 \leq g2$, a radius $R$ of curvature of the first curved surface and the second curved surface may be defined to satisfy a relationship of $g1 \leq R \leq g2$.

According to a fifth aspect of the present invention, the multileaf collimator according to the first aspect, when a gap $g1$ between two leaves, among the plurality of leaves, arranged side by side in the thickness direction and a gap $g2$ between the lateral surface of the depressed portion in a first one of the two leaves and the lateral surface of the protruded portion in a second one of the two leaves satisfy a relationship of $g2 \leq g1$, a radius $R$ of curvature of the first curved surface and the second curved surface may be defined to satisfy a relationship of g2≤R≤g1.

According to a sixth aspect of the present invention, there is provided a radiation treatment apparatus that includes the multileaf collimator according to any one of the first to fifth aspects and a radiation beam irradiation device that irradiates the multileaf collimator with a radiation beam.

Advantageous Effects of Invention

According to the above-described multileaf collimator and the radiation treatment apparatus, leakage of a radiation beam can be minimized while preventing occurrence of a crack or breakage in the leaves.

DESCRIPTION OF EMBODIMENTS

Figure 1:
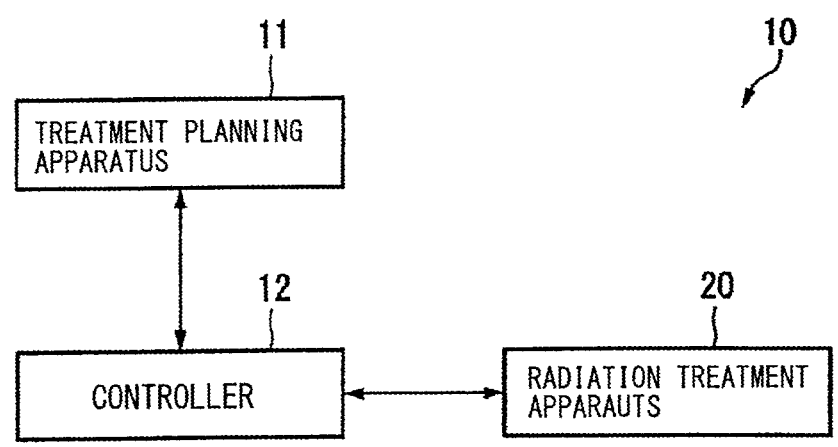
FIG. 1 A diagram showing a functional configuration of a radiation treatment system in an embodiment of this invention.

FIG. 1 is a diagram showing a functional configuration of a radiation treatment system 10 in an embodiment of this invention.

As shown in FIG. 1, the radiation treatment system 10 includes a treatment planning apparatus 11, a controller (a control unit) 12, and a radiation treatment apparatus 20.

The treatment planning apparatus 11 is an apparatus for receiving external inputs of properties of a radiation beam to be irradiated onto a patient (such as the intensity, a time period, an angle, a position, and a radiation region of the radiation beam to be irradiated onto the patient), and the properties are previously specified in accordance with details of a radiation treatment administered to the patient. The treatment planning apparatus 11 outputs various parameter values for control operation performed to radiate a radiation beam corresponding to the input properties of the radiation beam.

The controller 12 controls operation of the radiation treatment apparatus 20 based on the various parameter values generated in the treatment planning apparatus 11. The controller 12 is a computer device, such as a personal computer, that performs processing based on a predetermined program. The controller 12 is connected to the radiation treatment apparatus 20 through a wireless or wired communication line to enable bidirectional transmission of information.

Figure 2:
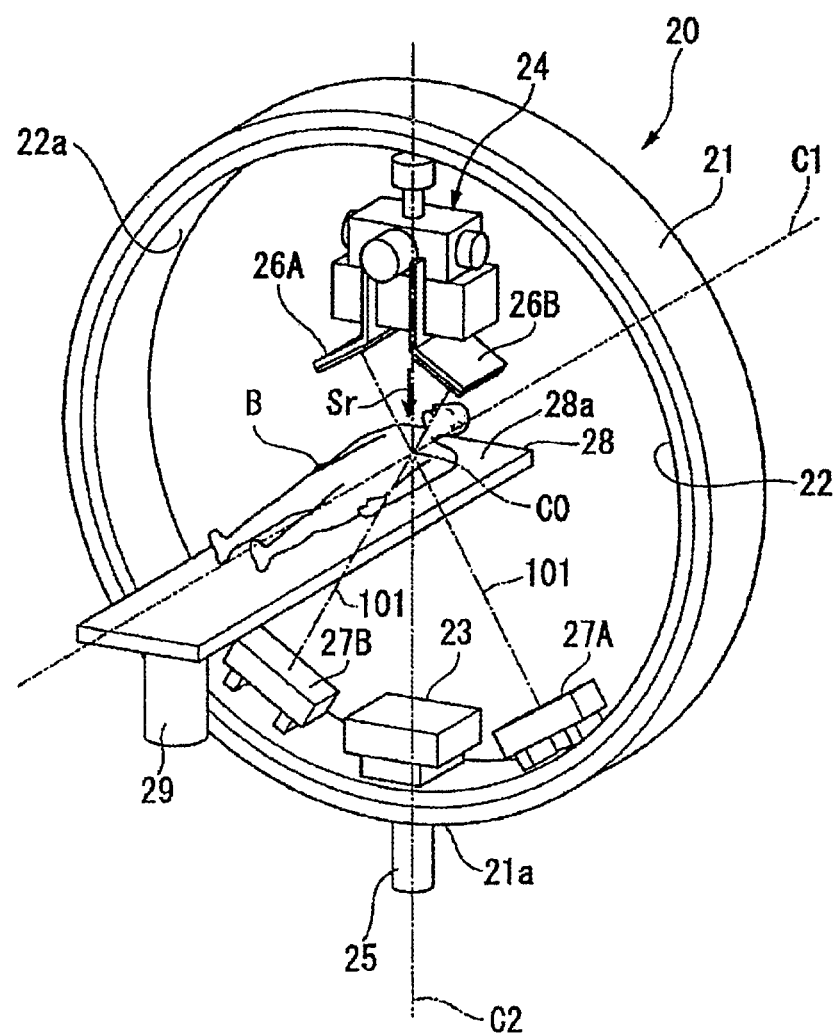
FIG. 2 A perspective view showing a schematic configuration of a radiation treatment apparatus which is a component of the radiation treatment system in the embodiment of this invention.

FIG. 2 is a perspective view showing a schematic configuration of the radiation treatment apparatus 20 which is a component of the radiation treatment system 10.

As shown in FIG. 2, the radiation treatment apparatus 20 is equipped with a ring frame 21, a traveling gantry 22, and a radiation beam irradiation device 24.

The ring frame 21 is formed in the shape of a cylinder which is circular in cross section. The ring frame 21 is disposed with a center axis C1 substantially aligned with a horizontal direction. In the ring frame 21, a rotating shaft 25 extending downward is integrally formed on an outer circumferential surface of the ring frame 21 at a lower end part 21a thereof. The rotating shaft 25 is supported by a base (not illustrated in the diagram) in a condition capable of rotating around a center axis C2 of the rotating shaft 25. The rotating shaft 25 is rotatably driven by a rotation drive mechanism (not illustrated). That is, the ring frame 21 is rotated about a vertical axis in conjunction with the rotating shaft 25 that is rotated by the rotation drive mechanism.

The traveling gantry 22 is formed in the shape of a cylinder which is circular in cross section. The traveling gantry 22 is arranged on an inner circumference side of the ring frame 21. The traveling gantry 22 is supported by the ring frame 21 and configured to be rotatable along an inner circumferential surface of the ring frame 21. In other words, the traveling gantry 22 shaped like a ring is able to rotate about the center axis C1 extending along the horizontal direction. The traveling gantry 22 is rotatably moved along a circumferential direction by a gantry drive mechanism (not shown).

The radiation beam irradiation device 24 emits a medical radiation beam Sr under control of the controller 12 (see FIG. 1). The radiation beam irradiation device 24 is supported on an inner circumferential surface 22a of the traveling gantry 22. The medical radiation beam Sr emitted from the radiation beam irradiation device 24 is adjusted so as to pass through an isocenter C0 which is an intersection point of the center axis C2 around which rotational movement of the ring frame 21 occurs and the center axis C1 around which rotational movement of the traveling gantry 22 occurs.

When the radiation beam irradiation device 24 is supported by the traveling gantry 22 as described above, the medical radiation beam Sr is always emitted so as to pass through the isocenter C0 irrespective of rotational movement of the ring frame 21 about the center axis C2 and rotational movement of the traveling gantry 22 about the center axis C1.

The radiation treatment apparatus 20 is further equipped with a sensor array 23. The sensor array 23 receives the medical radiation beam Sr, which has, after having been emitted from the radiation beam irradiation device 24, passed through an object existing in the vicinity of the isocenter C0, and generates a transmission image of the object. As the sensor array 23, an FPD (Flat Panel Detector), an X-ray II (Image Intensifier), or the like may be used.

Further, the radiation treatment apparatus 20 includes diagnostic X-ray sources 26A and 26B and sensor arrays 27A and 27B.

The diagnostic X-ray sources 26A and 26B are mounted in an inner circumferential side of the traveling gantry 22. The diagnostic X-ray sources 26A and 26B are arranged on both sides of the ring frame 21 in a circumferential direction across the center of the radiation treatment apparatus 20 (i.e. the center axis C2 of rotational movement of the ring frame 21). The diagnostic X-ray sources 26A and 26B are controlled by the controller 12 to emit a diagnostic X-ray 101 toward the isocenter C0. The diagnostic X-ray 101 is a circular cone beam which is conically spread from a point owned by each of the diagnostic X-ray sources 26A and 26B.

The sensor arrays 27A and 27B are supported on the inner circumferential surface 22a of the traveling gantry 22. The sensor arrays 27A and 27B are arranged so as to be opposed to the diagnostic X-ray sources 26A and 26B across the isocenter C0. The sensor arrays 27A and 27B receive the diagnostic X-ray 101, which has, after having been emitted from the diagnostic X-ray sources 26A and 26B, passed through the object existing in the vicinity of the isocenter C0, and generate transmission images of the object. As the sensor arrays 27A and 27B, for example, an FPD (Flat Panel Detector), an X-ray II (Image Intensifier), or the like may be used.

The radiation treatment apparatus 20 further includes a couch 28 and a couch actuator 29. The couch 28 has an upper surface 28a on which a patient B to be treated by the radiation treatment system 10 lies down horizontally.

The couch actuator 29 is controlled by the controller 12 to move the couch 28. The couch actuator 29 is supported by a base (not illustrated).

Figure 3:
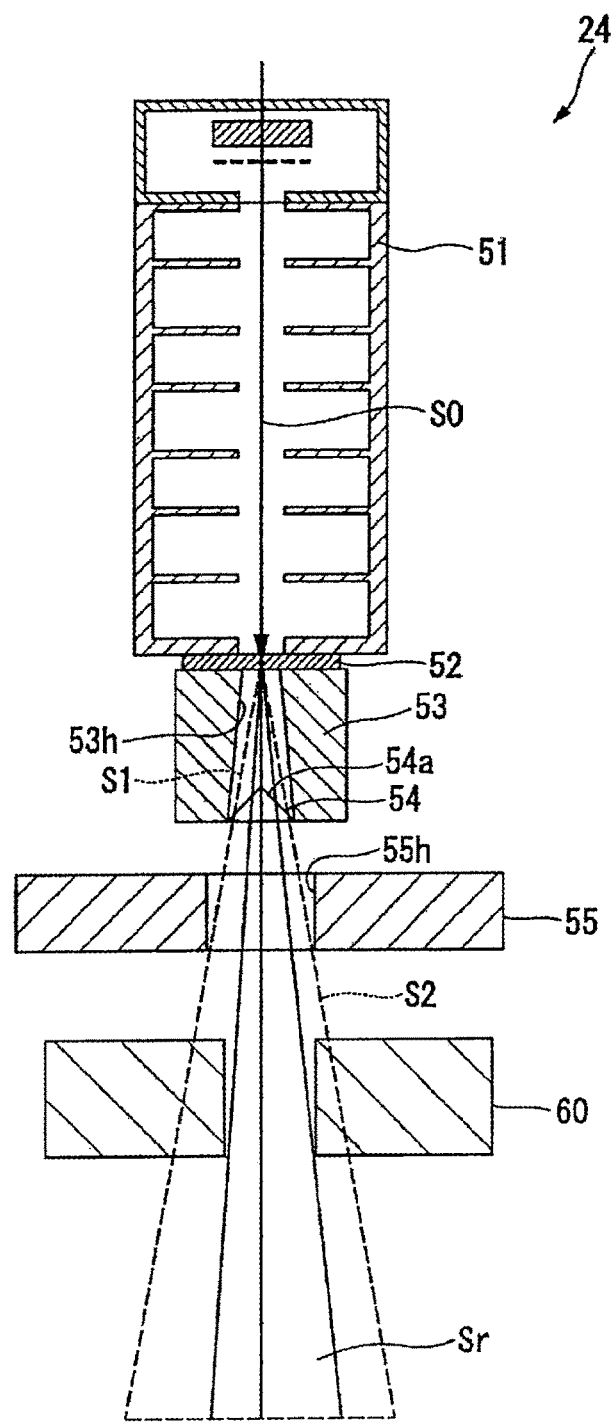
FIG. 3 A cross sectional view showing a radiation beam irradiation device in the embodiment of this invention.

FIG. 3 is a cross sectional view showing the radiation beam irradiation device 24 which is a component of the radiation treatment apparatus 20.

As shown in FIG. 3, the radiation beam irradiation device 24 includes an electron beam accelerator 51, an X-ray target 52, a primary collimator 53, a flattening filter 54, a secondary collimator 55, and a multileaf collimator 60.

The electron beam accelerator 51 irradiates the X-ray target 52 with an electron beam S0 generated by accelerating electrons.

The X-ray target 52 is formed of tungsten, a tungsten alloy, or other similar materials. The X-ray target 52 irradiated with the electron beam S0 emits a radiation beam S1.

The primary collimator 53 blocks a part of the radiation beam S1 to prevent regions other than a desired site from being irradiated with the radiation beam S1. The primary collimator 53 has a through hole 53h into with the radiation beam S1 emitted from the X-ray target 52 is directed to pass through. The primary collimator 53 is formed of lead, tungsten, or the like.

The flattening filter 54 is a filter that functions to substantially uniformly spread a dose of the radiation beam S1 on a plane perpendicular to a radiation direction of the radiation beam S1. The flattening filter 54 is formed of aluminum or the like. The flattening filter 54 is mounted on an exit side of the through hole 53h in the primary collimator 53. The flattening filter 54 has a substantially conical protrusion 54a oriented to point an X-ray target 52 side. The shape of the protrusion 54a is designed to make the dose of the radiation bean S1 spread substantially uniformly on the plane perpendicular to the radiation direction of the radiation beam S1.

The secondary collimator 55 blocks a part of the radiation beam S1. The secondary collimator 55 has, in its center region, a through hole 55h. The secondary collimator 55 allows a radiation beam S2 to pass only through the through hole 55h. The secondary collimator 55 is formed of lead, tungsten, or the like.

The radiation beam S2 whose intensity distribution is made uniform after passing through the primary collimator 53, the flattening filter 54, and the secondary collimator 55 described above is further blocked partially by the multileaf collimator 60. The multileaf collimator 60 is controlled by the controller 12 to regulate a field irradiated with the radiation beam S2. The multileaf collimator 60 generates the medical radiation beam Sr corresponding to the properties of the radiation beam to be irradiated onto the patient.

Figure 4:
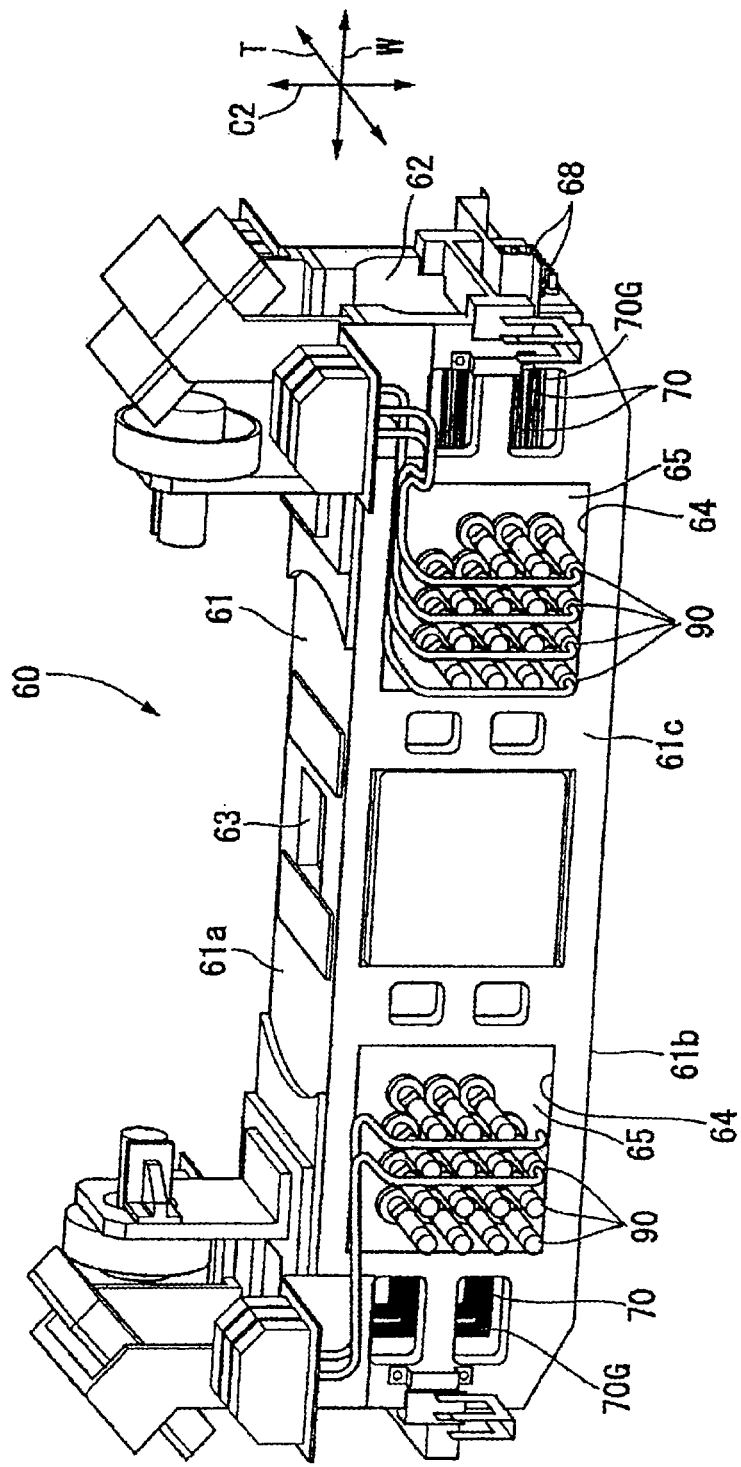
FIG. 4 A perspective view showing an outer appearance of a multileaf collimator constituting a part of the radiation beam irradiation device in the embodiment of this invention.
Figure 5:
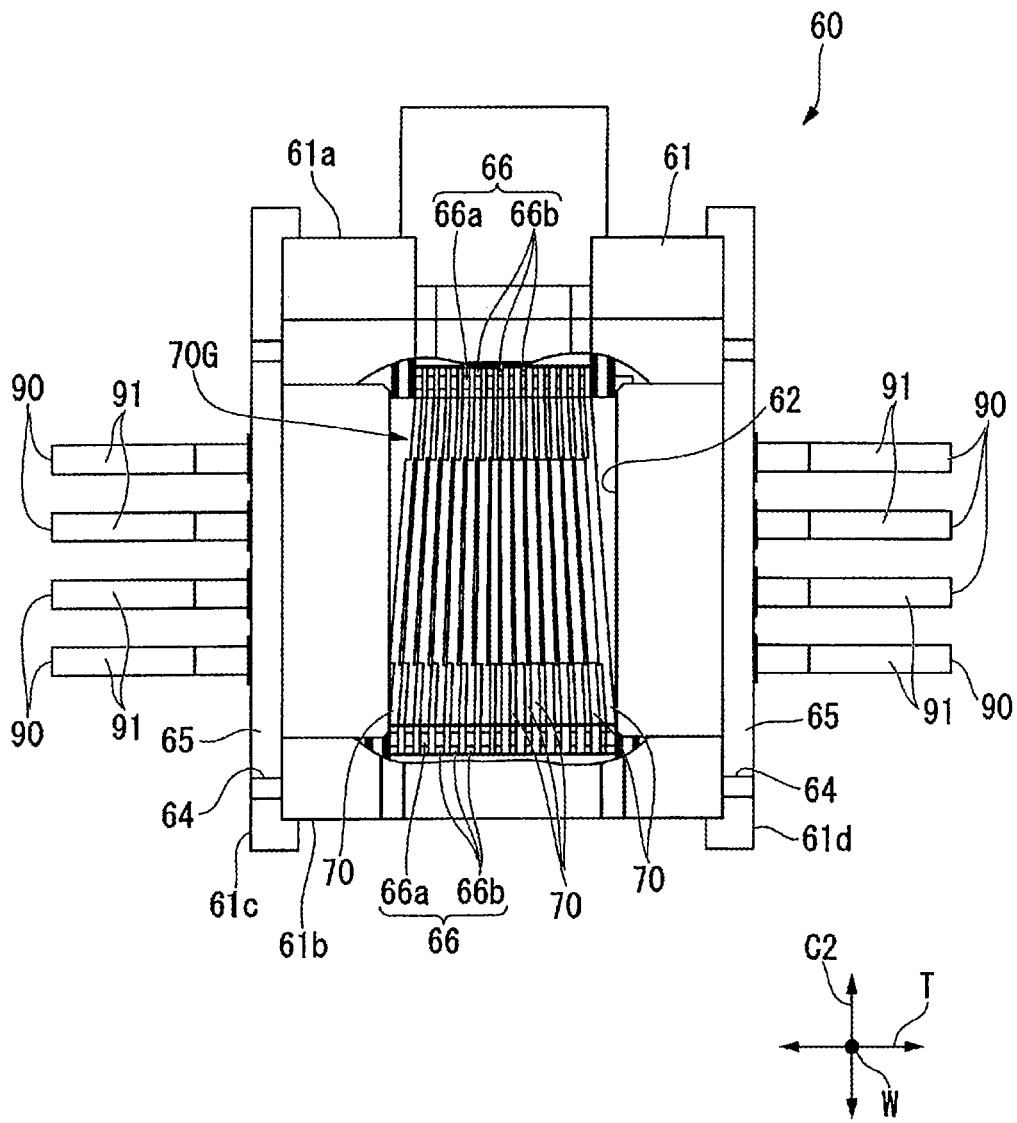
FIG. 5 A cross sectional view of the multileaf collimator in the embodiment of this invention taken along a width direction.
Figure 6:
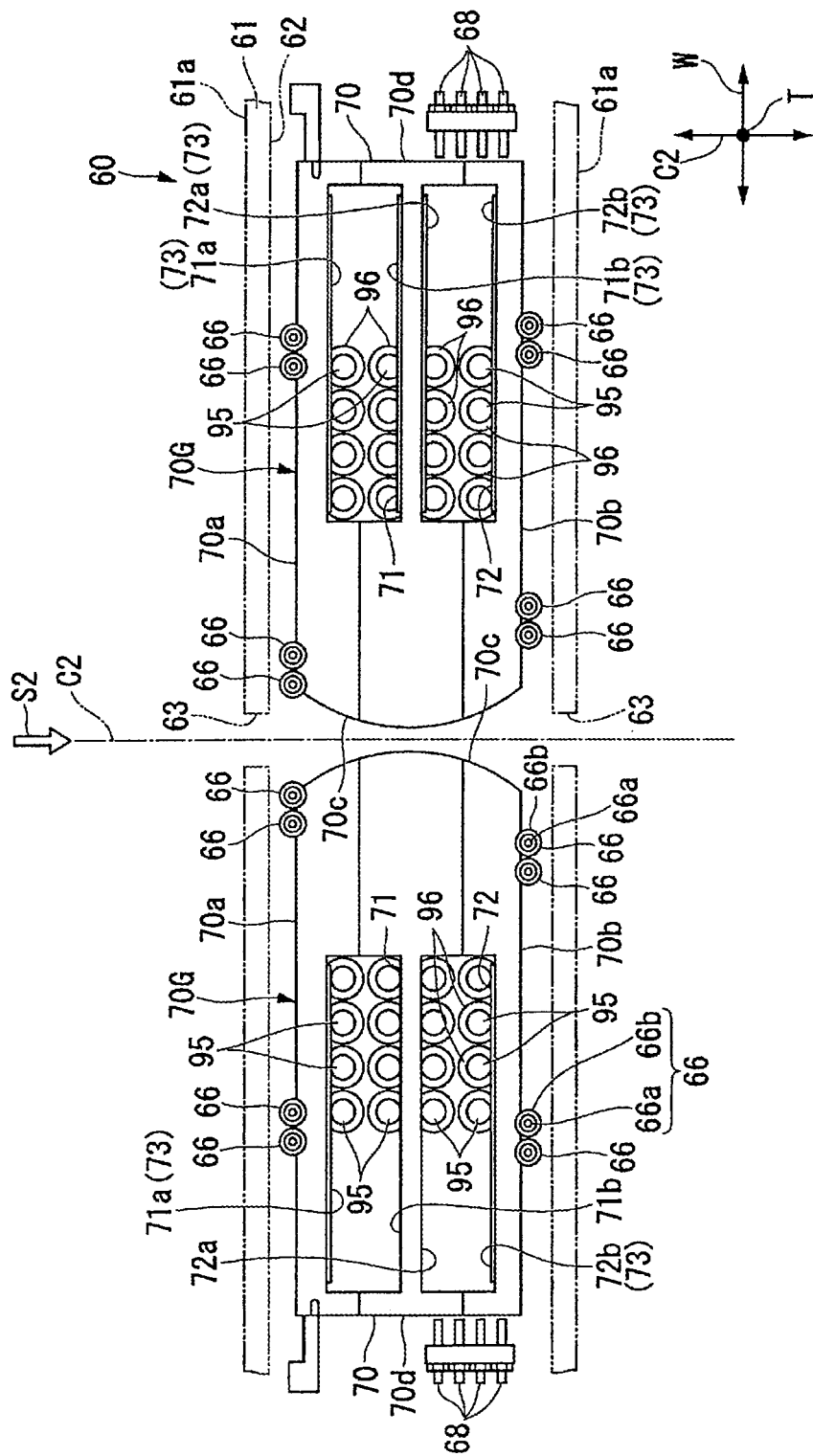
FIG. 6 A cross sectional view of the multileaf collimator in the embodiment of this invention taken along a direction perpendicular to a plate thickness direction of leaves.

FIG. 4 is a perspective view showing an outside appearance of the multileaf collimator 60 constituting a part of the radiation beam irradiation device 24. FIG. 5 is a cross sectional view of the multileaf collimator 60 taken along a width direction. FIG. 6 is a cross sectional view of the multileaf collimator 60 taken along a direction perpendicular to a second direction which is a direction along the thickness of a leaf 70 (hereinafter referred to as a plate thickness direction T).

As shown in FIGS. 4 to 6, the multileaf collimator 60 includes a frame 61, a plurality of leaves 70, and a drive device (driving mechanism) 90.

The frame 61 is formed in the shape of a rectangular box having longitudinal sides along one direction. The frame 61 is arranged in such a manner that a first direction (hereinafter referred to as a width direction W), which is a longitudinal direction of the frame 61, is orthogonal to a radiation beam irradiation axis of the radiation beam irradiation device 24. In the frame 61, a leaf housing part 62 is formed so as to be continuously hollow in the width direction W.

In the frame 61, openings 63, which penetrate outer peripheral sides of the frame 61 through the leaf housing part 62, are formed in both an upper surface part 61a located on a side of the frame 61 opposed to the radiation beam irradiation device 24 and a lower surface part 61b located on the other side from the upper surface part 61a (in FIG. 4, only one of the openings 63 defined in the upper surface part 61a is shown). The openings 63 are defined in center regions of the upper surface part 61a and the lower surface part 61b in the width direction W.

As shown in FIGS. 4 and 5, in the frame 61, rectangular openings 64, 64 are respectively formed in side surface parts 61c and 61d perpendicular to the upper surface part 61a and the lower surface part 61b. The openings 64 in the side surface part 61c and the openings 64 in the side surface part 61d are formed plane-symmetrically with respect to an imaginary plane located at the center between the side surface part 61c and the side surface part 61d. In the openings 64, rectangular base plates 65 are fitted. In this embodiment, an arrangement in which the openings 64 are formed in the frame 61 to mount the base plates 65 in the openings 64 is described by way of illustration. However, the embodiment is not limited to the disclosed arrangement. For example, the frame 61 may be integrally formed with the base plates 65 to eliminate the necessity of forming the openings 64 in the frame 61.

The leaves 70 are formed in the shape of substantially rectangular plates. The leaves 70 are formed of a material opaque to the radiation beam S2, such as, for example, tungsten, or a tungsten alloy.

As shown in FIG. 5, the leaves 70 are spaced apart from each other and arranged in a line along the plate thickness direction T. The leaves 70 constitute a leaf group 70G. The leaf group 70G in this embodiment consists of thirty leaves 70, for example. As shown in FIGS. 4 and 6, there are two leaf groups 70G formed as described above, and the two leaf groups 70G constitute a pair positioned within the leaf housing part 62 inside the frame 61 so as to be opposed to each other across a center region in the width direction W of the frame 61.

Figure 7:
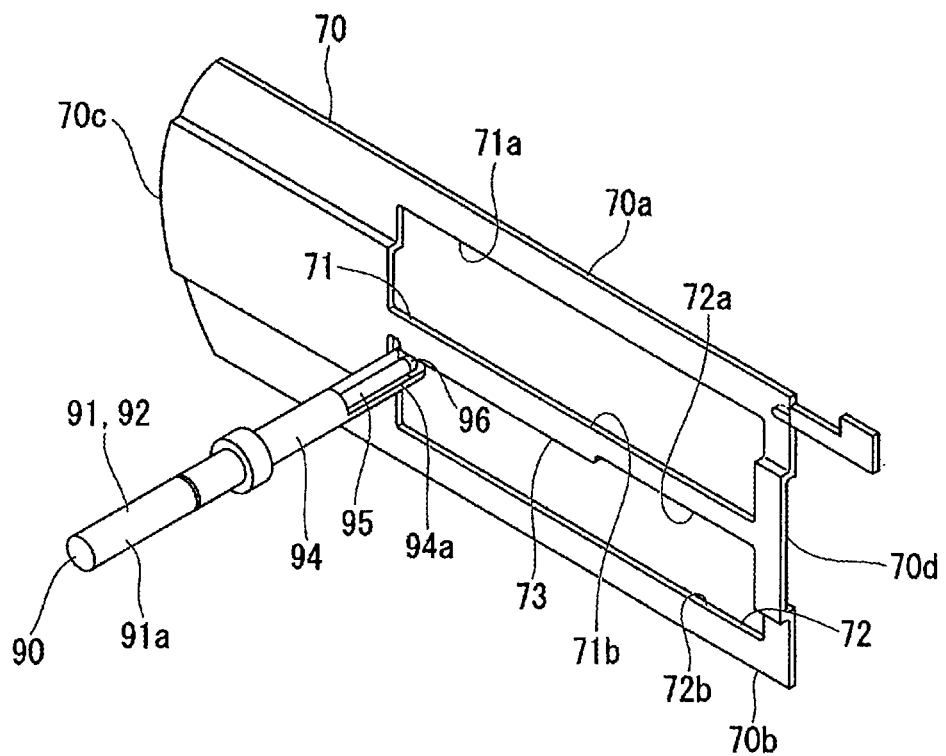
FIG. 7 A perspective view showing the leaves and a drive device for driving the leaves in the embodiment of this invention.
Figure 7:
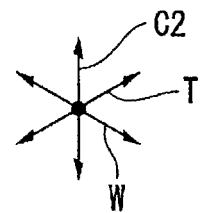

FIG. 7 is a perspective view showing a leaf 70 and a drive device 90 for driving the leaf 70.

As shown in FIGS. 6 and 7, the leaf 70 has a linear upper edge part (an end surface) 70a and a linear lower edge part 70b which are parallel to each other. As shown in FIG. 6, the upper edge part 70a is opposed, at a distance, to the upper surface part 61a in the leaf housing part 62. Similarly, in the leaf housing part 62, the lower edge part 70b is opposed, at a distance, to the lower surface part 61b.

The leaf 70 has a front edge part 70c which is outwardly curved in the shape of an arc on a side of the leaf 70 facing the center region in the width direction W of the frame 61 inside the leaf housing part 62. Further, the leaf 70 has a rear edge part 70d facing the outside of the frame 61 in the width direction W inside the leaf housing part 62, and the rear edge part 70d is formed in the shape of a line perpendicular to the upper edge part 70a and the lower edge part 70b.

The pair of two leaf groups 70G, 70G, which are opposed to each other across the center region along the width direction W within the leaf housing part 62, are arranged in such a manner that the front edge parts 70c of the leaves face a region defined between the opening 63 in the upper surface part 61a of the frame 61 and the opening 63 in the lower surface part 61b of the frame 61.

Each of the leaves 70 has slits 71 and 72 penetrating through the plate thickness direction T of the leaves 70. Each of the slits 71 and 72 is continuously formed along a direction of connecting the front edge part 70c to the rear edge part 70d in each of the leaves 70; i.e., the width direction W. The slits 71 and 72 are spaced apart from each other and arranged side by side along a direction of connecting the upper edge part 70a and the lower edge part 70b in each of the leaves 70. The slits 71 and 72 are formed at positions shifted from the front edge part 70c toward a rear edge part 70d side so as not to be irradiated with the radiation beam S2 incident from the opening 63 in the upper surface part 61a of the frame 61 into the leaf housing part 62 of the frame 61.

In each of the leaves 70, at least one of upper side edges 71a and 72a and lower side edges 71b and 72b of the slits 71 and 72 is equipped with a rack gear 73 continuously extending along the width direction W. Here, in the leaf group 70G, the rack gears 73 of adjacent leaves 70 located side by side along the direction in which the plurality of leaves 70 are arranged are mounted on different side edges selected from among the upper side edges 71a, 72a and the lower side edges 71b, 72b of the slits 71 and 72. In this way, pinion gears 96 engaging with the rack gears 73 of the adjacent leaves 70 and 70 in the plate thickness direction T can be prevented from interfering with each other.

The plurality of leaves 70 constituting each of the leaf groups 70G are supported by the frame 61. The frame 61 supports the plurality of leaves 70 in such a manner that the plurality of leaves are able to advance and retreat along the width direction W perpendicular to the plate thickness direction T. The frame 61 is equipped with slide support members 66. The slide support members 66 are arranged with a spacing along the width direction W on both an upper part and a lower part of each of the leaf groups 70G. In this embodiment, the upper part and the lower part in each of the leaf groups G are respectively equipped with two of the slide support members 66 for each of a center region side and an outer periphery side of the frame 61 in the width direction W, and therefore, each of the upper and lower parts includes a total of four of the slide support members 66 to guide movement of the leaves 70.

As shown in FIGS. 5 and 6, each of the slide support members 66 has a shaft 66a fixed to the frame 61 and a plurality of support rollers 66b, each of which is rotatably supported on the shaft 66a. The plurality of support rollers 66b are respectively disposed on positions corresponding to the plurality of leaves 70 constituting the leaf group 70G. The support rollers 66b are configured to be rotatable along a direction in which the upper edge parts 70a and the lower edge parts 70b of the leaves 70 are moved to advance.

As shown in FIG. 6, the upper edge part 70a and the lower edge part 70b of each of the leaves 70 are contacted by the support rollers 66b of the slide support members 66. At least two of the support rollers 66 are provided for each of the upper edge part 70a and the lower edge part 70b as the support rollers 66b making contact with the upper edge part 70a or making contact with the lower edge part 70b.

That is, the leaves 70 are supported via the slide support members 66 by the frame 61 in a state where each of the leaves 70 is independently advanceable or retreatable along the width direction W.

Here, in the above-described leaf group 70G, the adjacent leaves 70 and 70 located side by side in the plate thickness direction T may be designed to be respectively contacted by support rollers 66b contained in different ones of the above-described slide support members 66. This can prevent the support rollers 66b from interfering with each other between the adjacent leaves 70, 70. In this embodiment, the arrangement in which the leaves 70 are supported by the slide support members 66 equipped with the rotatable support rollers 66b has been described. However, the embodiment is not limited to the arrangement. For example, the leaves 70 may be slidably supported by means of slide support members 66 that are not rotated. In this case, the slide support members 66 may be provided, for example, with grooves in which the upper edge parts 70a and the lower edge parts 70b of the leaves 70 are slidably retained.

The frame 61 has a stopper 68 for limiting an amount of movement of each of the leaves 70 toward the rear edge part 70d side in the width direction W.

Figure 8:
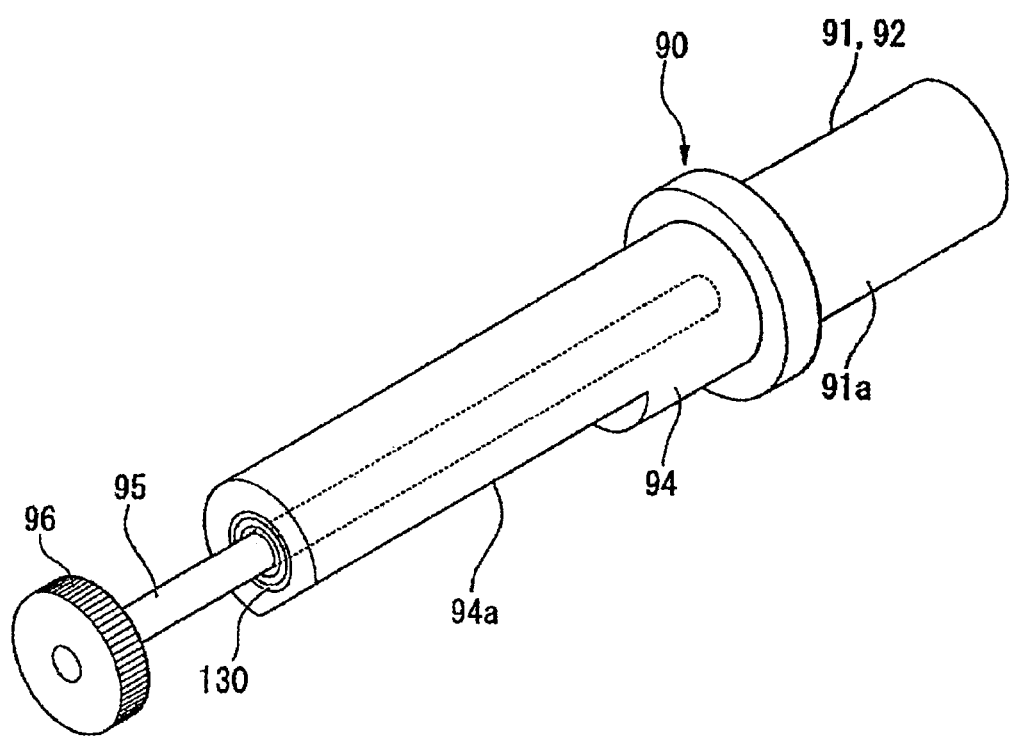
FIG. 8 A perspective view showing a configuration of the drive device in the embodiment of this invention.

FIG. 8 is a perspective view showing components of the drive device 90.

As shown in FIGS. 7 and 8, the drive device 90 is arranged for each of the plurality of leaves 70 and associated therewith. The drive device 90 includes a motor 91, a shaft 95, and a pinion gear 96.

The motor 91 is connected to a base end part of the shaft 95. The motor 91 actuates the shaft 95 to be rotated about an axis thereof.

Here, as shown in FIG. 5, the motors 91 are supported by the base plates 65 mounted along the side surface parts 61c and 61d of the frame 61.

The base plate 65 mounted on the side surface part 61c of the frame 61 supports the motors 91 in the drive devices 90 assigned to drive, among the plurality of leaves 70 constituting the leaf group 70G, half of the leaves 70 located on a side closer to the side surface part 61c. The base plate 65 mounted on the side surface part 61d of the frame 61 supports the motors 91 in the drive devices 90 assigned to drive, among the plurality of leaves 70 constituting the leaf group 70G, half of the leaves 70 located on a side closer to the side surface part 61d.

As shown in FIG. 7, the shaft 95 extends along the plate thickness direction T of the leaf 70. Further, as shown in FIGS. 6 and 7, the shaft 95 is inserted into the slits 71 or 72 of the plurality of leaves 70 in the leaf group 70G.

In addition, as shown in FIGS. 7 and 8, the pinion gear 96 is attached to a tip end part of the shaft 95. The pinion gear 96 is engaged with the rack gear 73 formed on any one of the upper side edges 71a and 72b and the lower side edges 71b and 72b, which constitute a part of the leaf 70, in the slits 71 and 72.

The drive device 90 further includes a rotary encoder 92 and a cover 94.

The rotary encoder 92 measures a rotation quantity of the shaft 95 and outputs measured results to the controller 12.

The cover 94 is formed in the shape of a hollow pipe. The cover 94 is integrally formed with a housing 91a of the motor 91. A bearing 130 is attached to an end part of the cover on an opposite side from the motor 91. In addition, the shaft 95 is inserted into the cover 94. The shaft 95 is rotatably supported by the bearing 130. In other words, the cover 94 supports the shaft 95 via the bearing 130 at a position spaced apart from the motor 91 along an extending direction of the shaft 95. In this way, deformation of the shafts 95 caused by a self weight or other factors is prevented from occurring, to ensure that the pinion gear 96 is reliably engaged with teeth of the rack gear 73 even when the motor 91 is located away from the leaf 70.

In the cover 94, a notch 94a is formed on a part of a circumferential direction.

The notch 94a is provided to prevent the cover 94, to which the notch 94a is provided, from interfering with leaves 70 located on a motor 91 side of the cover 94 relative to the leaf 70 having the rack gear 73 that is engaged with the pinion gear 96 of the shaft 95 inserted into the cover 94 to which the notch 94a is provided.

In the drive device 90 as described above, the motor 91 is actuated under control of the controller 12 to rotate the shaft 95. Rotation of the shaft 95 causes the pinion gear 96 to be rotated together with the shaft 95 whose rotating force is transferred to the rack gear 73. Then, the leaf 70 equipped with the rack gear 73 is shifted along an advancing or retreating direction which corresponds to the width direction W.

In each of the two leaf groups 70G coupled as a pair, when the leaves 70 constituting the leaf groups 70G are individually advanced or retreated along the width direction W as described above, the radiation beam S2 incident from the opening 63 on the upper surface part 61a of the frame 61 is partially blocked by the leaves 70 in the leaf groups 70G on both sides of the opening 63. In other words, the multileaf collimator 60 functions to produce the medical radiation beam Sr adjusted to have the shape corresponding to a predetermined field of irradiation.

Figure 9:
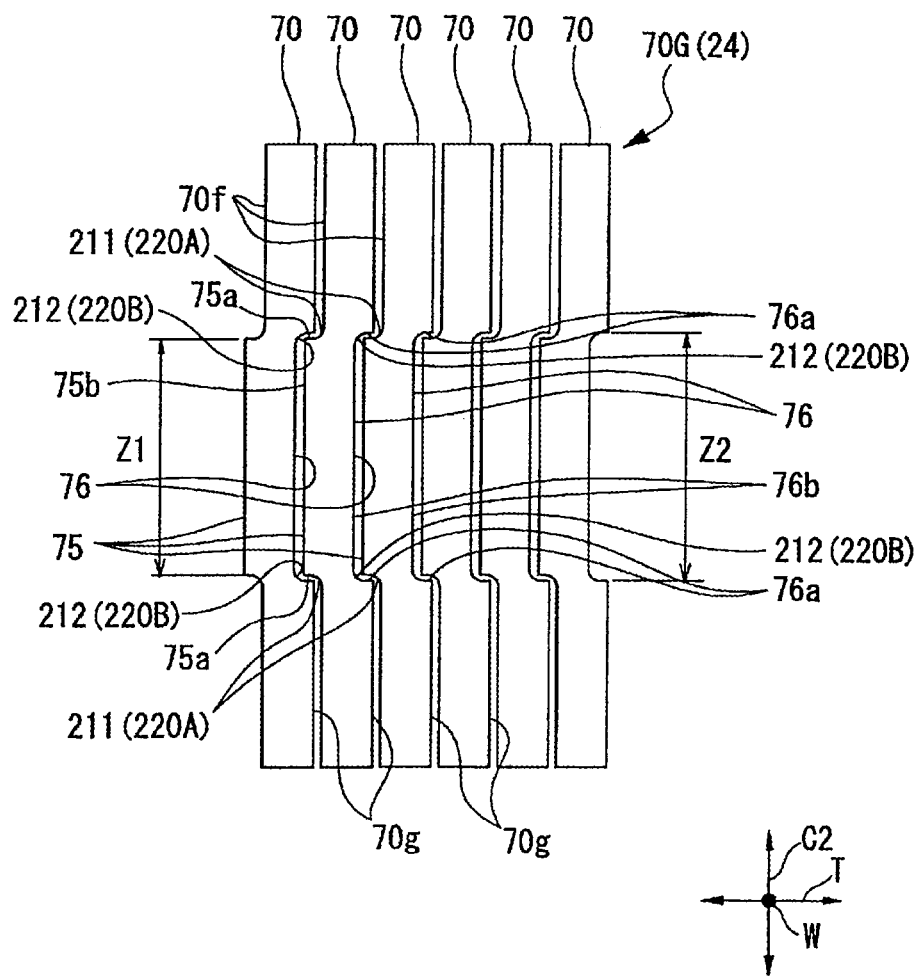
FIG. 9 A diagram showing the shape of the leaves in the embodiment of this invention.
Figure 10:
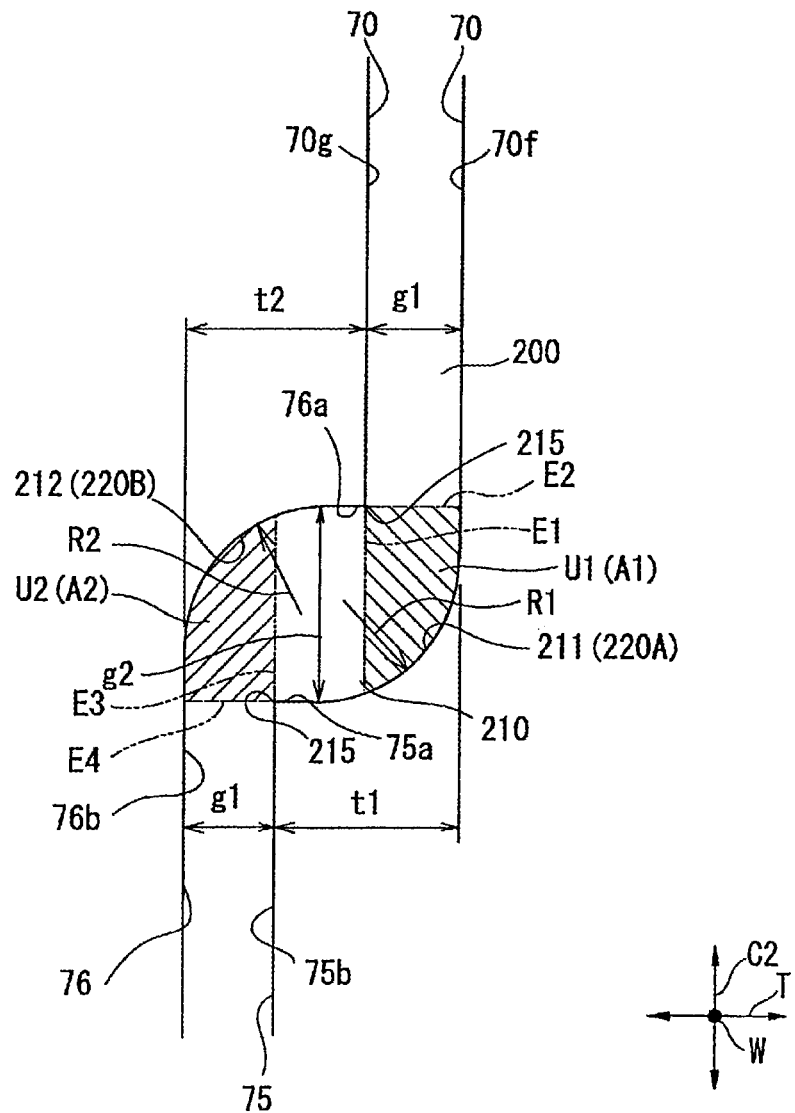
FIG. 10 An enlarged view showing regions opposed to each other in two leaves within a leaf group in the embodiment of this invention.

FIG. 9 is a diagram showing the shape of the leaves. FIG. 10 is an enlarged view showing regions of two leaves in the leaf group opposed to each other.

As shown in FIG. 9, each of the plurality of leaves 70 constituting each of the leaf groups 70G has a protruded portion 75 and a depressed portion 76.

The protruded portion 75 is formed on a surface 70f which is a first side in the plate thickness direction T of the leaf 70. The protruded portion 75 is continuously formed along the width direction W. The protruded portion 75 has a pair of lateral surfaces 75a and 75a and a top surface 75b. The lateral surfaces 75a are designed to be perpendicularly raised from the surface 70f. The pair of lateral surfaces 75a are formed so as to be spaced apart from each other in a vertical direction of connecting the upper edge part 70a and the lower edge part 70b. The top surface 75b is formed in parallel with the surface 70f to connect the lateral surfaces 75a, 75a.

In addition, a corner part 211 where the surface 70f intersects with each of the lateral surfaces 75a of the protruded portion 75 is designed as a curved surface (a first curved surface) 220A having a predetermined radius R1 of curvature.

The depressed portion 76 is formed on a surface 70g which is a second side in the plate thickness direction T of the leaf 70. The depressed portion 76 is continuously defined along the width direction W. The depressed portion 76 has a pair of lateral surfaces 76a and a bottom surface 76b. The lateral surfaces 76a are extended perpendicular to the surface 70f toward a surface 70f side. The pair of lateral surfaces 76a are formed so as to be spaced apart from each other in the vertical direction of connecting the upper edge part 70a and the lower edge part 70b. The bottom surface 76b is formed in parallel with the surface 70f to connect the pair of lateral surfaces 76a.

Further, a corner part 212 where the surface 70g intersects with each of the lateral surfaces 76a is designed as a curved surface (a second curved surface) 220B having a predetermined radius R2 of curvature.

A center position between the pair of lateral surfaces 75a of the protruded portion 75 and a center position between the pair of the lateral surfaces 76a of the depressed portion 76 are defined to be located substantially at the same position in the vertical direction of the leaf 70. Further, a distance Z1 between the pair of lateral surfaces 75a is defined to be smaller than a distance Z2 between the pair of lateral surfaces 76a.

In the leaf group 70G, the two leaves 70 (hereinafter, referred to as a first leaf 70 and a second leaf 70, respectively) adjacent to each other in the plate thickness direction T are positioned in such a manner that the surface 70f of the first leaf 70 and the surface 70g of the second leaf 70 are opposed to each other. In the first leaf 70 and the second leaf 70 adjacent to each other in the plate thickness direction T, the protruded portion 75 of the first leaf 70 is accommodated in the depressed portion 76 of the second leaf 70.

As shown in FIG. 10, the first leaf 70 and the second leaf 70 adjacent to each other are disposed side by side with a predetermined gap g1 along the plate thickness direction T. In this way, in-between the two leaves 70, a gap space 200 is created with a bending section 210 which is bent in a cranked geometry between the protruded portion 75 and the depressed portion 76.

The radiation beam S2 emitted from the radiation beam irradiation device 24 travels into the gap space 200. In addition to traveling along a straight line within the gap space 200, the radiation beam S2 may propagate downward while being scattered by both lateral surfaces in the gap space 200.

Therefore, in order to prevent leakage of the radiation beam S2 propagating through the gap space 200 downward of the leaf group 70G, the gap g1 in the plate thickness direction T between the two leaves 70 and 70 is defined, for example, as follows:

$$0 < g1 \leq 1.0 \text{ mm}$$

Further, the radius R1 of curvature of the corner part 211 at the intersection of the surface 70f and the lateral surface 75a of the protruded portion 75 and the radius R2 of curvature of the corner part 212 at the intersection of the lateral surface 76a and the bottom surface 76b in the depressed portion 76 are defined as follows:

$$0<R1\leq 1.0 \text{ mm, and } 0<R2\leq 1.0 \text{ mm}$$

Still further, a bending angle at each of the corner parts 211 and 212 is greater than or equal to 60°, and preferably equal to approximately 90° (for example, 85° ~95°).

Moreover, when the radius R1 of curvature of the corner part 211 and the radius R2 of curvature of the corner part 212 are excessively great, there is a possibility that the radiation bean S2 may leak through the gap space 200 and downwardly propagate to regions below the leaf group 70G. With this in view, the radius R1 of curvature of the corner part 211 and the radius R2 of curvature of the corner part 212 are preferably designed to be two times or less of a level difference dimension t1 between the top surface 75b of the protruded portion 75 and the surface 70f and two times or less of a level difference dimension t2 between the bottom surface 76b of the depressed portion 76 and the surface 70g, respectively.

Further, in the bending section 210, when any one of the radius R1 of curvature of the corner part 211, the radius R2 of curvature of the corner part 212, the gap g1 in the plate thickness direction T between the leaves 70 adjacent to each other along the plate thickness direction T, and the gap g2 in the vertical direction (the radiation direction of the radiation beam S2) between the lateral surface 75a of the protruded portion 75 and the lateral surface 76a of the depressed portion 76 is excessively great, there is the possibility that the radiation beam S2 may leak through the gap space 200.

Accordingly, the radii R1 and R2 of curvature and the gaps g1 and g2 are specified, for example, as described below. In the description below, it is assumed for the sake of simplicity that the radius R1 of curvature=the radius R2 of curvature=the radius R of curvature.

(a) When the gap g1≤the gap g2, the radius R of curvature of the corner part 211 and of the corner part 212 is defined to be smaller than or equal to the gap g1 (R≤g1).

In this case, the dose D of the radiation beam that is scattered within the gap space 200 and leaked therefrom is defined as follows:

$$D \propto A1 \times A2 \quad (1)$$

In the above expression, "A1" represents an area of a scattering region U1 enclosed by the surface 70f of the leaf 70, the lateral surface 75a of the protruded portion 75, an extension line E1 from the surface 70g opposed to the surface 70f across the gap space 200, and an extension line E2 from the lateral surface 76a of the depressed portion 76 opposed to the lateral surface 75a across the gap space 200. Further, "A2" represents an area of a scattering region U2 enclosed by the bottom surface 76b of the depressed portion 76 in the leaf 70, the lateral surface 76a of the depressed portion 76 in the leaf 70, an extension line E3 from the top surface 75b of the protruded portion 75 opposed to the bottom surface 76b across the gap space 200, and an extension line E4 from the lateral surface 75a of the protruded portion 75.

When the corner parts 211 and 212 are designed to maintain the right angle rather than being formed as the curved surfaces 220A and 220B having the radius R of curvature, the dose D is defined as follows:

$$D \propto A1 \times A2 \propto (g1+g2)^2 \quad (2)$$

As opposed to this, when the corner parts 211 and 212 are formed as the curved surfaces 220A and 220B having the radius R of curvature, the dose D is defined as follows:

$$D \propto A1 \times A2 \propto (g1+g2-2R \times (1-\pi/4))^2 \quad (3)$$

This means that the dose D of the leaked radiation beam can be reduced by forming the corner parts 211 and 212 in the shape of the curved surfaces 220A and 220B having the radius R of curvature.

(b) In a case of g2≤g1, the radius R of curvature of the corner parts 211 and 212 is defined to be smaller than or equal to the gap g2 (R≤g2).

When the corner parts 211 and 212 are designed to maintain the right angle rather than being formed as the curved surfaces 220A and 220B having the radius R of curvature, the dose D is defined as follows:

$$D \propto A1 \times A2 \propto (g1+g2)^2 \quad (2)$$

As opposed to this, when the corner parts 211 and 212 are formed as the curved surfaces 220 A and 220B having the radius R of curvature, the dose D is defined as follows:

$$D \propto A1 \times A2 \propto (g1+g2-2R \times (1-\pi/4))^2 \quad (3)$$

This means that the dose D of the leaked radiation beam can be reduced by forming the corner parts 211 and 212 in the shape of the curved surfaces 220A and 220B having the radius R of curvature.

(c) In a case of g1≤g2, the radius R of curvature of the corner parts 211 and 212 is defined to have a relationship of g1≤R≤g2.

When the corner parts 211 and 212 are designed to maintain the right angle rather than being formed as the curved surfaces 220A and 220B having the radius R of curvature, the dose D is defined as follows:

$$D \propto A1 \times A2 \propto (g1+g2)^2 \quad (2)$$

As opposed to this, when the corner parts 211 and 212 are formed as the curved surfaces 220A and 220B having the radius R of curvature, the dose D is defined as follows:

$$D \propto A1 \times A2 \propto (g2-R+R \cdot \cos^{-1}((R-g1)/R))^2 \quad (4)$$

This means that the dose D of the leaked radiation beam can be reduced by forming the corner parts 211 and 212 in the shape of the curved surfaces 220A and 220B having the radius R of curvature.

(d) In a case of g2≤g1, the radius R of curvature of the corner parts 211 and 212 is defined to have a relationship of g2≤R≤g1.

When the corner parts 211 and 212 are designed to maintain the right angle rather than being formed as the curved surfaces 220A and 220B having the radius R of curvature, the dose D is defined as follows:

$$D \propto A1 \times A2 \propto (g1+g2)^2 \quad (2)$$

As opposed to this, when the corner parts 211 and 212 are formed as the curved surfaces 220A and 220B having the radius R of curvature, the dose D is defined as follows:

$$D \propto A1 \times A2 \propto (g1-R+R \cdot \cos^{-1}((R-g2)/R))^2 \quad (5)$$

This means that the dose D of the leaked radiation beam can be reduced by forming the corner parts 211 and 212 in the shape of the curved surfaces 220A and 220B having the radius R of curvature.

(e) In a case of g1≤g2, the curved surfaces 220A and 220B of the corner parts 211 and 212 are designed to be respectively located outside of circles drawn with a radius r in the range of 0<r<g1 around apexes 215 which are inwardly located in bending directions and opposed to the corner parts 211 and 212. In this way, the dose of the scattered beam can be reduced.

(f) In a case of g2≤g1, the curved surfaces 220A and 220B of the corner parts 211 and 212 are designed to be respectively located outside of circles drawn with a radius r in the range of 0<r<g2 around the apexes 215 which are inwardly located in the bending directions and opposed to the corner parts 211 and 212. In this way, the dose of the scattered beam can be reduced.

In the radiation treatment system 10 as described above, a treatment is performed as described below.

First, a user secures a patient B on the couch 28 of the radiation treatment apparatus 20 in a posture indicated in a treatment plan that is input into the treatment planning apparatus 11.

The controller 12 activates the rotation drive mechanism (not shown in the drawing) and a gantry drive device (not shown). More specifically, the controller 12 causes the ring frame 21 and the travelling gantry 22 to rotate around the center axes C1 and C2 for moving the radiation beam irradiation device 24 to irradiate a position of an affected site in the patient B with the medical radiation beam Sr at an irradiation angle indicated in the treatment plan. Further, the controller 12 causes each of the drive devices 90 to advance or retreat corresponding one of the leaves 70 for changing the shape of a field irradiated with the medial radiation beam Sr while being regulated by the multileaf collimator 60 into the shape indicated in the treatment plan input into the treatment planning apparatus 11.

Then, the controller 12 uses the radiation beam irradiation device 24 to irradiate the affected site of the patient B with the medial radiation beam Sr at the dose indicated in the treatment plan input into the treatment planning apparatus 11.

According to the multileaf collimator 60 in the above-described embodiment, because the curved surfaces 220A and 220B are respectively formed between the surface 70f of the leaf 70 and the lateral surface 75a of the protruded portion 75 and between the surface 70g and the lateral surface 76a of the depressed portion 76, stress is not easily concentrated on any portion of the leaf 70. Therefore, cracking and breakage can be prevented from occurring while reducing leakage of the radiation beam S2.

In addition, leakage of the radiation beam S2 can be reliably minimized by appropriately setting the radii R1 and R2 of curvature of the curved surfaces 220A and 220B based on the gasp g1 and g2 between the two leaves 70 arranged side by side in the plate thickness direction T.

Modification Example of Embodiment

Although the corner part 211 at the intersection of the surface 70f of the leaf 70 and each of the lateral surfaces 75a of the protruded portion 75 and the corner part 212 at the intersection of the surface 70g and the lateral surface 76a are designed as the curved surfaces 220A and 220B, the embodiment is not limited to such geometry.

Figure 11:
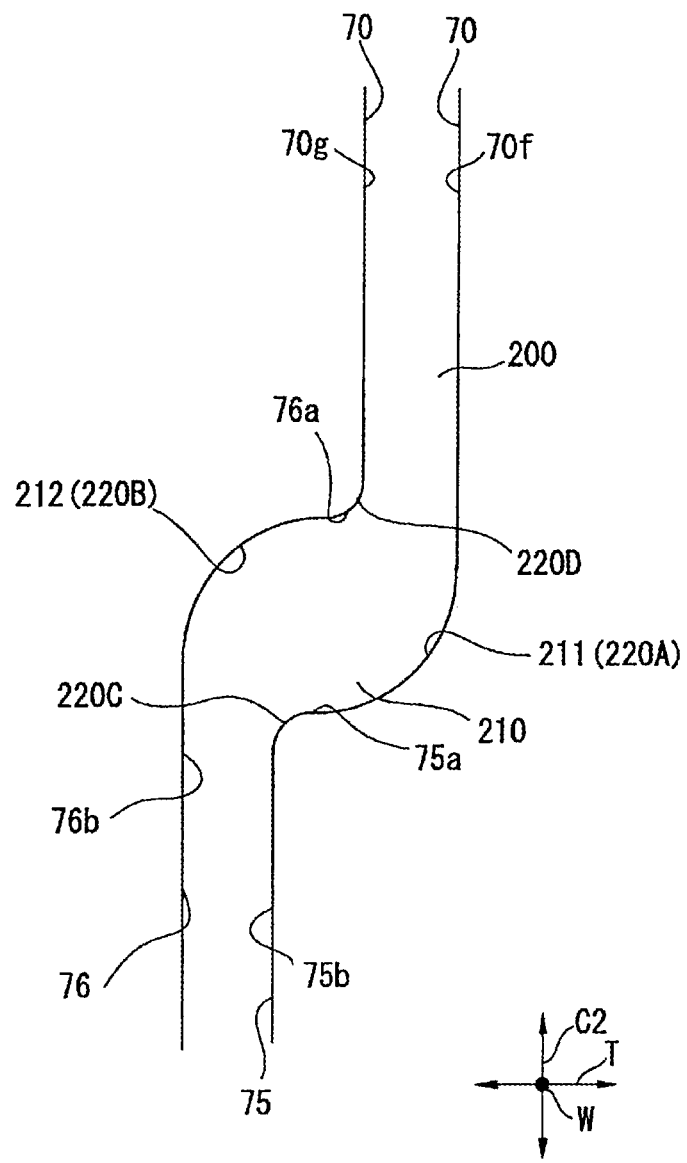
FIG. 11 A diagram showing a modification example of the embodiment of this invention in an exposed view.

FIG. 11 is a diagram showing a modification example of the leaf illustrated in the above embodiment.

As shown in FIG. 11, curved surfaces 220C and 220D having a predetermined radius of curvature may be formed in the leaf 70 between the lateral surface 75a and the top surface 75b of the leaf 70 and between the lateral surface 76a of the depressed portion 76 and the surface 70g of the leaf 70.

Other Embodiments

The present invention is not limited to the above-described embodiment, and may be modified in design without departing from the gist of the invention.

INDUSTRIAL APPLICABILITY

When the first curved surface is formed between the first side surface of the leaf and the lateral surface of the protruded part and the second curved surface is formed between the second side surface of the leaf and the lateral surface of the depressed portion, leakage of the radiation beam can be minimized while preventing cracking and breakage from occurring in the leaf.

REFERENCE SIGNS LIST 10 radiation treatment system
11 treatment planning apparatus
12 controller
20 radiation treatment apparatus
21 ring frame
21a lower end part
22 travelling gantry
22a inner circumferential surface
23 sensor array
24 radiation beam irradiation device
25 rotating shaft
26A, 26B source
27A, 27B sensor array
28 couch
28a upper surface
29 couch actuator
51 electron beam accelerator
52 X-ray target
53 primary collimator
53h through hole
54 flattening filter
54a protrusion
55 secondary collimator
55h through hole
60 multileaf collimator
61 frame
61a upper surface part
61b lower surface part
61c, 61d side surface part
62 leaf housing part
63 opening
64 opening
65 base plate
66 slide support member
66a shaft
66b support roller
68 stopper
70 leaf
70G leaf group
70a upper edge part
70b lower edge part
70c front edge part
70d rear edge part
70f surface
70g surface
71, 72 slit
71a, 72a upper side edge
71b lower side edge
73 rack gear 75 protruded portion
75a lateral surface
75b top surface
76 depressed portion
76a lateral surface
76b bottom surface
90 drive device
91 motor
91a housing
92 rotary encoder
94 cover
95 shaft
96 pinion gear
101 X-ray
130 bearing
200 gap space
210 bending section
211 corner part
212 corner part
215 apex
220A curved surface (first curved surface)
220B curved surface (second curved surface)
220C curved surface
220D curved surface
B patient
C0 isocenter
C1 center axis
C2 center axis
E1, E2, E3, E4 extension line
g1 gap
g2 gap
P circle
Q circle
R radius of curvature
r radius
R1 radius of curvature
R2 radius of curvature
S0 electron beam
S1 radiation beam
S2 radiation beam
Sr medical radiation beam
T plate thickness direction
t1 level difference dimension
t2 level difference dimension
U1 scattering region
U2 scattering region
W width direction
Z1 distance
Z2 distance
θ1 intersection angle
θ2 intersection angle

The invention claimed is:

1. A multileaf collimator for regulating a range irradiated with a radiation beam, comprising:
 a plurality of leaves arranged along a thickness direction, wherein
 each of the plurality of leaves comprising;
  a protruded portion protrudingly formed on a first side surface in a plate thickness direction of the leaf,
  a depressed portion formed in a second side surface in the plate thickness direction of the leaf, and configured to receive insertion of the protruded portion formed on another one of the plurality of leaves,
  a first curved surface formed between the first side surface of the leaf and a lateral surface of the protruded portion, and
  a second curved surface formed between the second side surface of the leaf and a lateral surface of the depressed portion.

2. The multileaf collimator according to claim 1, wherein:
 when a gap g1 between two leaves, among the plurality of leaves, the two leaves being positioned side by side in the thickness direction, and a gap g2 between the lateral surface of the depressed portion in a first one of the two leaves and the lateral surface of the protruded portion in a second one of the two leaves satisfy a relationship of:

$g1 < g2$, a radius R of curvature of the first curved surface and the second curved surface satisfies a relationship of:

$R \leq g1$.

3. The multileaf collimator according to claim 1, wherein:
 when a gap g1 between two leaves, among the plurality of leaves, the two leaves being positioned side by side in the thickness direction, and a gap g2 between the lateral surface of the depressed portion in a first one of the two leaves and the lateral surface of the protruded portion in a second one of the two leaves satisfy a relationship of:

$g2 \leq g1$, a radius R of curvature of the first curved surface and the second curved surface satisfies a relationship of:

$R \leq g2$.

4. The multileaf collimator according to claim 1, wherein:
 when a gap g1 between two leaves, among the plurality of leaves, the two leaves being positioned side by side in the thickness direction and a gap g2 between the lateral surface of the depressed portion in a first one of the two leaves and the lateral surface of the protruded portion in a second one of the two leaves satisfy a relationship of:

$g1 \leq g2$, a radius R of curvature of the first curved surface and the second curved surface satisfies a relationship of:

$g1 \leq R \leq g2$.

5. The multileaf collimator according to claim 1, wherein when a gap g1 between two leaves, among the plurality of leaves, the two leaves being positioned side by side in the thickness direction and a gap g2 between the lateral surface of the depressed portion in a first one of the two leaves and the lateral surface of the protruded portion in a second one of the two leaves satisfy a relationship of:

$g2 \leq g1$, a radius R of curvature of the first curved surface and the second curved surface satisfies a relationship of:

$g2 \leq R \leq g1$.

6. A radiation treatment apparatus, comprising:
 the multileaf collimator according to claim 1, and
 a radiation beam irradiation device that irradiates the multileaf collimator with the radiation beam.

* * * * *